United States Patent [19]
Kawaguchi et al.

[11] Patent Number: 5,921,948
[45] Date of Patent: Jul. 13, 1999

[54] SURGICAL DRESSING

[75] Inventors: Hiroko Kawaguchi; Yoshifumi Hosaka; Saburo Otsuka, all of Ibaraki, Japan

[73] Assignee: Nitto Denko Corporation, Osaka, Japan

[21] Appl. No.: 08/755,342

[22] Filed: Nov. 22, 1996

[30] Foreign Application Priority Data

Dec. 12, 1995 [JP] Japan .................................. 7-346857

[51] Int. Cl.$^6$ ........................................................ A61F 5/00
[52] U.S. Cl. .................. 602/52; 602/42; 602/54
[58] Field of Search ................... 602/41–59; 604/180

[56] References Cited

U.S. PATENT DOCUMENTS 2,858,830  11/1958  Robins ...................................... 602/41

*Primary Examiner*—Richard J. Apley
*Assistant Examiner*—Kim Lee
*Attorney, Agent, or Firm*—Sughrue, Mion, Zinn, Macpeak & Seas, PLLC

[57] ABSTRACT

A surgical dressing comprising a pressure-sensitive adhesive tape which comprises a polytetrafluoroethylene film support having provided thereon a pressure-sensitive adhesive layer, in which the polytetrafluoroethylene film support is a uniaxially stretched porous film and the adhesive tape has a load at 50% extension of not lower than 50 g/15 mm and lower than 200 g/15 mm. The surgical dressing does not involve irritation and can be applied with easy stretch to even the part of the body having a special contour, such as the tip of a finger or a joint, with good adhesion and can follow the movement of the part to which it is stuck.

4 Claims, No Drawings

SURGICAL DRESSING

FIELD OF THE INVENTION

This invention relates to a surgical dressing which is stuck to the skin to cover and protect cuts, agnails, regenerated skin, etc. against water, dust, bacteria, and shocks, such as an adhesive tape and an adhesive bandage.

BACKGROUND OF THE INVENTION

Various adhesive tapes and adhesive bandages have widely been used as surgical dressings. If a tape uses a nonporous film as a support, the moisture from the skin is prevented from evaporating through the support to cause a hot and uncomfortable feel and creates a rash or irritation. Therefore the support of these surgical dressings, particularly adhesive bandages, usually has pores for air passage so as not to interfere with cutaneous respiration, by which to alleviate discomfort and a rash. However, use of a porous support is not enough to prevent discomfort and a rash. Another problem to consider is that the dressing as stuck to the skin tends to be peeled or lifted from the skin owing to failure to follow the extension and contraction of a joint, etc. If a dressing fails to follow the movement of the skin, water or dust unavoidably gets in through the gaps at edges of the tape or through the pores of the support. It follows that if the support of the dressing or an absorbent pad of an adhesive bandage remains wet, an uncomfortable feel, a rash, an eruption, itching, and the like gradually occurs.

Because the surgical dressing is to be applied to the skin, development of the dressing requires consideration of non-irritation to the skin and flexibility to follow the movement o f the skin.

JP-A-U-6-13821 (the term "JP-A-U" as used herein means an unexamined published Japanese utility model application) provides a tape for medical use in which a synthetic resin film having flexibility and moderate water vapor permeability is used as a support so as to make the tape follow the movement of the body, prevent tightening up of the tape as applied to the skin, and give a comfortable feel (as applied) to the wearer.

JP-B-U-6-47456 (the term "JP-B-U" as used herein means an examined published Japanese utility model application) discloses an adhesive bandage comprising a support made of stretchable nonwoven fabric for application over a relatively large wound at bending sites of the body, such as elbows and knees.

However, the tape of JP-A-U-6-13821 is unsatisfactory in applicability and adhesion to the skin, especially to a part of the body having a special shape, such as the tip of a finger or a joint, on account of the relatively high tensile strength of its support (load at 50% extension: 200 to 900 g/15 mm). That is, the synthetic resin film support is not deemed to achieve deformability in conformity to the special contour of a site of application, such as the tip of a finger or a joint, to provide intimate adhesion making no gaps.

The nonwoven fabric used in JP-B-U-6-47456 has no water repellency and will easily allow water to soak into when used in contact with water. It is likely, as stated above, that discomfort and such symptoms as a rash, an eruption, and itching may result.

The JP-A-U-6-13821 reference refers to polyethylene, polypropylene, polybutene, polystyrene, etc. as examples of the synthetic resin constituting the support. It is specified that the synthetic resin film support has a load of at least 200 g/15 mm at 50% extension to secure sufficient nerve (i.e., bending stiffness) for application to the skin. However, a tape having a load at 50% extension of 200 g/15 mm or more is deflected when it is wound around, for example, a finger to make a gap only to provide poor adhesion to the skin. Further, such a tape as applied hardly follows the movement of the site of application, e.g., a joint. Therefore, the tape has unsatisfactory windability around such a part of the body as a special contour, for example, the tip of a finger or a joint. That is, the proposed synthetic resin film support is not deemed to achieve the object that the tape be wound around an affected part of the body with intimate adhesion and no gap. If the load of the synthetic resin film support at 50% extension is below 200 g/15 mm, the tape would be wound around in an arbitrary manner while being stretched. However, as long as the synthetic resin film disclosed in JP-A-U-6-13821 is used, the tape would have insufficient bending stiffness and be difficult to stick to the skin.

SUMMARY OF THE INVENTION

An object of the present invention is to provide a surgical dressing such as an adhesive tape for medical use and an adhesive bandage which functions as a adhesive plaster, which has satisfactory applicability and a comfortable feel as applied to the skin, that is, which does not cause discomfort or a rash and swell as manifestations of irritation when stuck to the skin for extended time periods or when wetted with water as applied, which is conforming to fit over a part of the body having a special contour, such as the tip of a finger and a joint, with easy stretch, and which can follow the movement of the site of application, such as extension and contraction of a joint, and therefore be kept free from peeling, lifting or tightening while worn.

The inventors have extensively studied a synthetic resin film as a support of a surgical dressing that has moderate bending stiffness for easy application to the skin and can be wound over an affected site of the body in an arbitrary manner. They have found as a result that the object of the invention is accomplished by using, as a support, a porous film comprising a uniaxially stretched polytetrafluoroethylene (hereinafter abbreviated as PTFE) film and adjusting the load of the adhesive tape at 50% extension to 50 g/15 mm or higher and lower than 200 g/15 mm.

The invention provides an adhesive tape for medical use which comprises a polytetrafluoroethylene film support having provided thereon a pressure-sensitive adhesive layer, in which the polytetrafluoroethylene film support is a uniaxially stretched porous film and the adhesive tape has a load at 50% extension of not lower than 50 g/15 mm and lower than 200 g/15 mm.

The adhesive tape of the invention preferably has a residual stress rate of not more than 90% after 5 seconds from 50% extension or not more than 75% after 60 seconds from 50% extension. The term "50% extension" means extending the adhesive tape to 1.5 times the original length.

The adhesive tape of the invention preferably has a water vapor permeability of at least 300 g/m$^2$/24 hr. The upper limit thereof is generally 4,000 g/m$^2$/24 hr.

The invention also provides an adhesive bandage comprising the above-described adhesive tape, which additionally has an absorbent pad on the pressure-sensitive adhesive layer side thereof.

DETAILED DESCRIPTION OF THE INVENTION

The load at 50% extension of the adhesive tape should not be lower than 50 g and lower than 200 g per 15 mm width.

If it is higher than 200 g/15 mm, the tape fails to follow the movement of the part of the body to which it is stuck, especially a joint, etc. and also undergoes deflection when wound a round a joint, etc. due to insufficient deformability only to provide poor adhesion to the skin. If the load at 50% extension is lower than 50 g/15 mm, the load required for extension of the adhesive tape, though made of a PTFE porous film, is too small to secure bending stiffness for easy application.

The load at 50% extension per 15 mm width is measured in the following manner. An adhesive tape is cut into a 15 mm wide and 80 mm long strip along the direction perpendicular to the direction of stretching. The width direction of the strip corresponds to the direction of stretching. The central 40 mm length of the specimen prepared is extended at a pulling rate of 100 mm/min, and the load when the length is extended to a 60 mm length (50% extension) is taken as a load at 50% extension.

In practicing the present invention, it is desirable for the adhesive tape to have a residual stress rate of not more than 90% after 5 seconds from 50% extension or not more than 75% after 60 seconds from 50% extension. If the adhesive tape has too high a residual stress, the dressing causes tension of the skin and peeling, lifting or tightening of the dressing while it is worn, giving an uncomfortable feel to the wearer. The residual stress as referred to above is obtained from equation:

Residual Stress Rate (%)=(B/A)×100 wherein A is a load (g/15 mm) at 50% extension, i.e., at the time when an adhesive tape is extended to reach 50% extension, and B is a load (g/15 mm) after t seconds from 50% extension, i.e., at the time when the adhesive tape subjected to 50% extension is left to stand at the 50% extended state for t seconds.)

The PTFE porous film is prepared by uniaxially stretching a film made of PTFE. A preferred thickness of the PTFE porous film is from 20 to 200 μm.

A PTFE film can be made porous by, for example, preparing an uniaxially stretched film from PTFE containing a foaming agent and heating the film to cause foaming as described in JP-B-42-13560 and JP-B-51-18991 (the term "JP-B" as used herein means an examined Japanese Patent publication). The PTFE porous film, while not particularly limited in diameter of its micropores or the number of pores per unit area, is preferably designed to have a water vapor permeability of from 2000 to 10000 g/m²/24 hrs, particularly from 3000 to 6000 g/m²/24 hr. If the water vapor permeability of the PTFE porous film is smaller than 2000 g/m²/24 hrs, the tape tends to cause rashes due to stuffiness. If it is higher than 10000 g/m²/24 hr, the film has reduced strength as a support and tends to be cut when pulled. The terminology "water vapor permeability" as used for a support means a value measured in accordance with JIS Z 0208 under condition A.

The adhesive tape for medical use according to the invention comprises the above-described support made of a PTFE porous film having formed on at least one side thereof a pressure-sensitive adhesive layer. The pressure-sensitive adhesive layer is not particularly limited as long as the pressure-sensitive adhesive is not irritating and medically acceptable. Suitable pressure-sensitive adhesives include acrylic pressure-sensitive adhesives mainly comprising an alkyl (meth)acrylate; rubber pressure-sensitive adhesives comprising polyisobutylene, polyisoprene, polybutadiene, a styrene-isoprene(or butadiene)-styrene block copolymer, etc.; vinyl ether pressure-sensitive adhesives mainly comprising a vinyl alkyl ether; and silicone pressure-sensitive adhesives mainly comprising polyorganosiloxane.

The pressure-sensitive adhesive layer preferably has a thickness of 20 to 100 μm.

The PTFE porous film with the pressure-sensitive adhesive layer thereon has a water vapor permeability of 100 to 4000 g/m²/24 hr. The terminology "water vapor permeability" as used for a support with a pressure-sensitive adhesive layer thereon means a value measured in accordance with JIS Z 0208 under condition B.

The adhesive tape for medical use according to the invention is not particularly limited by method of preparation. It can be prepared by, for example, applying a pressure-sensitive adhesive solution to a separator (release sheet) to form a pressure-sensitive adhesive layer and laminating the pressure-sensitive adhesive layer and the PTFE porous film support through contact bonding. A pressure-sensitive adhesive solution may be applied directly to a support and dried.

The adhesive tape may have any form, such as a cut sheet form, a roll form or a band form. The adhesive tape may be used as an adhesive bandage for medical use. If desired, an absorbent pad (such as that made of gauze) can be provided on the surface of the pressure-sensitive adhesive side of the tape such that the absorbent pad covers the affected part such as cuts or regenerated skin.

If desired, a drug may be incorporated into the pressure-sensitive adhesive layer, or a drug-containing layer may be provided independently. Suitable drugs include analgesic antiinflammatory agents, antimicrobials, antifungals, antihypertensive agents, antibiotics, and vitamins.

It is desirable for the surgical dressing of the invention to have unidirectional extensibility and water repellency as well as water vapor permeability. The former function is effective in making the dressing not only follow the movement or extension of the skin but also tighten up moderately. The latter function is to inhibit penetration of water with which the dressing contacts.

Since the surgical dressing of the invention comprises a uniaxially stretched PTFE porous film as a support and the adhesive tape has a load at 50% extension of not lower than 50 g/15 mm and lower than 200 g/15 mm, it exhibits sufficient bending stiffness for easy application to the skin and deformability with ease stretch in winding along the contour of the site of application, especially such a part making a complicated movement as a joint or such a fine part as the tip of a finger, in an arbitrary manner with intimate adhesion and no gaps.

The use of the PTFE porous film as a support provides a surgical dressing endowed with improved flexibility over conventional dressings comprising a nonwoven or woven fabric support. Having water repellency and being a uniaxially oriented film, the PTFE porous support can be applied with easy stretch over an affected part of the body, even such a part making a complicated movement as a joint or such a fine part as the tip of a finger, in conformity to the contour of the part.

Where the adhesive tape has a residual stress rate of not more than 90% after 5 seconds from 50% extension, particularly not more than 75% after 60 seconds from 50% extension, the surgical dressing does not cause tension of the skin, or peeling, lifting or tightening of the dressing while it is worn.

The present invention will be illustrated in greater detail with reference to Examples, but it should be understood that the invention is not construed as being limited thereto.

EXAMPLE 1

A 60 μm thick PTFE porous film having micropores and unidirectional extensibility was prepared. Separately an acrylic pressure-sensitive adhesive was applied to a separator so as to provide a thickness of 40 μm. The PTFE porous film was stuck to the pressure-sensitive adhesive layer side to obtain an adhesive tape of the invention.

EXAMPLE 2

An adhesive tape was obtained in the same manner as in Example 1, except for replacing the acrylic pressure-sensitive adhesive with a rubber pressure-sensitive adhesive.

EXAMPLE 3

An adhesive tape was obtained in the same manner as in Example 1, except for replacing the acrylic pressure-sensitive adhesive with a vinyl ether pressure-sensitive adhesive.

EXAMPLE 4

An adhesive tape was obtained in the same manner as in Example 1, except for replacing the acrylic pressure-sensitive adhesive with a silicone pressure-sensitive adhesive.

EXAMPLE 5

An adhesive tape was obtained in the same manner as in Example 1, except for increasing the thickness of the PTFE porous film to 120 μm and the thickness of the acrylic pressure-sensitive adhesive layer to 60 μm.

EXAMPLE 6

An adhesive tape was obtained in the same manner as in Example 1, except for reducing the thickness of the PTFE porous film to 30 μm and the thickness of the acrylic pressure-sensitive adhesive layer to 20 μm.

EXAMPLES 7 TO 10

An adhesive tape was obtained in the same manner as in Example 1, except for changing the thickness of the acrylic pressure-sensitive adhesive layer to 20, 60, 80 or 100 μm.

Comparative Example 1

An adhesive tape was obtained in the same manner as in Example 1, except for using a porous polyethylene film in place of the PTFE porous film.

Comparative Example 2

An adhesive tape was obtained in the same manner as in Example 1, except for using nonwoven fabric in place of the PTFE porous film.

Comparative Example 3

An adhesive tape was obtained in the same manner as in Example 1, except for increasing the thickness of the PTFE porous film to 160 μm and the thickness of the acrylic pressure-sensitive adhesive layer to 100 μm.

Comparative Example 4

An adhesive tape was obtained in the same manner as in Example 1, except for reducing the thickness of the PTFE porous film to 20 μm and the thickness of the acrylic pressure-sensitive adhesive layer to 20 μm.

The adhesive tapes for medical use prepared in Examples 1 to 6 and Comparative Examples 1 to 4 were evaluated in terms of load at 50% extension, residual stress rate, water vapor permeability, comfort in use, and the like in accordance with the following test methods. The results obtained are shown in Table 1 below.

(1) Load at 50% Extension

The adhesive tape was cut into a 15 mm wide and 80 mm long strip in the direction perpendicular to the direction of stretching. The central 40 mm length of the specimen was extended at a pulling rate of 100 mm/min by means of a tensile tester (TENSILON/STM-T-50BP), and the load at which the length was extended to a 60 mm length (50% extension) was measured.

(2) Residual Stress Rate

The adhesive tape was allowed to stand as 50% extended as in (1) above. The load at a 5-second period and a 60-second period from the 50% extension was read from the record on the chart to calculate the residual stress rate (%).

(3) Applicability

The adhesive tape was cut into a 20 mm wide and 100 mm long strip and wound round the tip and the first interphalangeal joint of 6 persons. The applicability was evaluated as follows.

(a) Windability (Adhesion)

An adhesive tape that can be wound round the tip of a finger and the joint with intimate adhesion and no gap was judged "good", while a tape that forms gaps and unevenness due to the gaps on winding was judged "poor".

(b) Feel of Use

An adhesive tape which, as stuck to the skin, does not give a feel of tension nor come off the skin when the finger is bent was judged "good". An adhesive tape that gives a feel of tension and in some cases comes off the skin on bending the finger was judged "poor".

(c) Water Repellency

An adhesive tape showing water repellency when in contact with water was judged "good", while an adhesive tape that gets wet with water was judged "poor".

(d) Tightening

An adhesive tape that does not tighten up when wound around a finger was judged "good", while an adhesive tape that tightens up to give an unpleasant feel was judged "poor".

(4) Water Vapor Permeability

The water vapor permeability of the adhesive tape was measured according to JIS Z $0208_{-1976}$ under condition B (Temperature: 40±0.5° C., Relative Humidity: 90±2%). The water vapor permeability of the PTFE support alone was measured according to JIS Z $0208_{-1976}$ under condition A (Temperature: 25±0.5° C., Relative Humidity: 90±2).

TABLE 1

| Example No. | Load at 50% Extension (g/15 mm) | Residual Stress Rate (%) 5 sec. | 60 sec. | Applicability to the Skin (a) | (b) | (c) | (d) | Water vapor Permeability of Adhesive Tape (g/m²/24 hr) | Water vapor Permeability of of Support (g/m²/24 hr) |
|---|---|---|---|---|---|---|---|---|---|
| Example 1 | 108 | 71 | 54 | good | good | good | good | 586 | 4823 |
| Example 2 | 109 | 71 | 53 | good | good | good | good | 432 | " |
| Example 3 | 105 | 70 | 50 | good | good | good | good | 623 | " |
| Example 4 | 98 | 69 | 52 | good | good | good | good | 2134 | " |
| Example 5 | 180 | 73 | 55 | good | good | good | good | 425 | 4241 |
| Example 6 | 55 | 65 | 48 | good | good | good | good | 1233 | 5362 |
| Comparative Example 1 | 440 | 79 | 68 | poor | good | good | good | 563 | — |
| Comparative Example 2 | 630 | 90 | 71 | poor | good | poor | good | 634 | — |
| Comparative Example 3 | 220 | 75 | 58 | poor | poor | good | good | 243 | 4016 |
| Comparative Example 4 | 45 | 62 | 45 | good | good | good | good* | 1315 | 5673 |

Note: *Having no bending stiffness and difficult to apply.

As is apparent from Table 1, the adhesive tapes of Examples exhibited excellent applicability in terms of windability, feel of use, water repellency and non-tightening as compared with Comparative Examples. Even though a PTFE porous film was used as a support, the adhesive tape of Comparative Example 3, which had a load at 50% extension of not less than 200 g/15 mm, underwent deflection on winding to cause gaps and poor adhesion to the skin and failed to follow the bending movement of a joint, etc. The adhesive tape of Comparative Example 4, whose load at 50% extension was less than 50 g/15 mm, had insufficient bending stiffness and was difficult to apply to the skin.

Adhesive tapes for medical use were then prepared by using a 60 μm thick PTFE porous film support and applying an acrylic pressure-sensitive adhesive to a thickness varying from 20 to 100 μm. The resulting adhesive tapes had a water vapor permeability ranging from about 200 to 1300 g/m²/24 hr. Applicability of the adhesive tapes was evaluated in terms of feel of use and irritation to the skin according to the following test methods. The load at 50% extension was also measured. In practicing the evaluation, the adhesive tapes obtained in Examples 1 and 7 to 10 were tested. The load at 50% extension of these adhesive tapes fell within a range of not less than 50 g/15 mm and less than 200 g/15 mm. The results of evaluation are shown in Table 2 below.

Test Methods for Evaluation
(1) Feel of Use

The adhesive tape was cut into a 20 mm wide and 50 mm long piece, stuck to the chest of 6 persons for consecutive 3 days, and was given scores for feel of use and irritation to the skin based on the following standard everyday. The sum of the scores was divided by the number of testing persons to give the average.

Standard of evaluation of the feel of use
1 . . . Satisfactory
2 . . . Itching was sometimes experienced.
3 . . . Itching was continuously experienced.
4 . . . Itching continued.

(2) Skin Irritation

Evaluation of irritation to the skin was conducted according to the Japanese Standard of a patch test (Japan Contact Dermatitis Research Group):
2 . . . An erythema and an edema or a papule (++)
1 . . . An obvious erythema (+)
0.5 . . . A slight erythema (+–)
0 . . . No reaction (–)

TABLE 2

| Example No. | Thickness of Pressure-sensitive Adhesive Layer (μm) | Water Vapor Permeability (g/m²/24 hr) | Load at 50% Extension (g/15 mm) | Feel of Use 1st Dy | 2nd Dy | 3rd Dy | Skin Irritation 0 Hr | 1 Hr | 24 Hr |
|---|---|---|---|---|---|---|---|---|---|
| Example 1 | 40 | 586 | 108 | 1.0 | 1.0 | 1.3 | 0.1 | 0.2 | 0.0 |
| Example 7 | 20 | 1225 | 97 | 1.0 | 1.0 | 1.2 | 0.1 | 0.2 | 0.0 |
| Example 8 | 60 | 425 | 112 | 1.0 | 1.1 | 1.4 | 0.2 | 0.3 | 0.1 |
| Example 9 | 80 | 313 | 117 | 1.0 | 1.2 | 1.4 | 0.2 | 0.4 | 0.2 |
| Example 10 | 100 | 240 | 123 | 1.0 | 1.2 | 1.6 | 0.3 | 0.5 | 0.2 |

It is seen from Table 2 that adhesive tapes for medical use preferably have a load at 50% extension of not lower than 50 g/15 mm and lower than 200 g/15 mm and a water vapor permeability of at least 300 g/m²/24 hr. While subject to variation depending to the kind of the adhesive used, the upper limit of water vapor permeability is about 1250 g/m²/24 hr for endowing the tape with bending stiffness to secure strength.

As can be seen from the results of Example 4, use of a silicone pressure-sensitive adhesive provides an adhesive tape which is particularly excellent for medical use in that the water vapor permeability is very satisfactory and the load at 50% extension is as low as 98 g/15 mm.

As has been fully described, since the adhesive tape of the invention comprises a uniaxially stretched PTFE porous film as a support and has a load at 50% extension of not lower than 50 g/15 mm and lower than 200 g/15 mm, it exhibits sufficient bending stiffness for easy application to the skin and deformability with ease stretch in winding along the contour of the site of application, especially such a part making a complicated movement as a joint or such a fine part as the tip of a finger, in an arbitrary manner with intimate adhesion.

While the invention has been described in detail and with reference to specific examples thereof, it will be apparent to one skilled in the art that various changes and modifications can be made therein without departing from the spirit and scope thereof.

What is claimed is:

1. A surgical dressing comprising an adhesive tape, said adhesive tape comprising a polytetrafluoroethylene film support having provided thereon a pressure-sensitive adhesive layer, wherein said polytetrafluoroethylene film support is a uniaxially stretched porous film and said adhesive tape has a tensile strength at 50% extension of not lower than 50 g/15 mm and lower than 200 g/15 mm.

2. The surgical dressing of claim 1, wherein said adhesive tape has a residual stress rate of not more than 90% after 5 seconds from 50% extension or not more than 75% after 60 seconds from 50% extension.

3. The surgical dressing of claim 1, wherein said adhesive tape has a water vapor permeability of at least 300 g/m$^2$/24 hr.

4. The surgical dressing of claim 1, further comprising an absorbent pad on a side thereof having said pressure-sensitive adhesive layer thereon.

* * * * *